United States Patent
Yates et al.

(10) Patent No.: US 9,943,377 B2
(45) Date of Patent: Apr. 17, 2018

(54) METHODS, SYSTEMS, AND DEVICES FOR CAUSING END EFFECTOR MOTION WITH A ROBOTIC SURGICAL SYSTEM

(71) Applicant: Ethicon Endo-Surgery, LLC, Guaynabo, PR (US)

(72) Inventors: David C. Yates, West Chester, OH (US); Frederick E. Shelton, IV, Hillsboro, OH (US); Jason L. Harris, Lebanon, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 0 days.

(21) Appl. No.: 15/237,648

(22) Filed: Aug. 16, 2016

(65) Prior Publication Data
US 2018/0049812 A1 Feb. 22, 2018

(51) Int. Cl.
| | | |
|---|---|---|
| *G05B 19/19* | (2006.01) | |
| *A61B 34/30* | (2016.01) | |
| *A61B 17/295* | (2006.01) | |
| *F16H 19/00* | (2006.01) | |
| *B25J 15/02* | (2006.01) | |
| *A61B 46/10* | (2016.01) | |

(52) U.S. Cl.
CPC ............ *A61B 34/30* (2016.02); *A61B 17/295* (2013.01); *B25J 15/0213* (2013.01); *F16H 19/001* (2013.01); *A61B 46/10* (2016.02); *A61B 2034/305* (2016.02)

(58) Field of Classification Search
CPC ............ A61B 34/30; A61B 34/70; B25J 9/12
See application file for complete search history.

(56) References Cited

U.S. PATENT DOCUMENTS

| | | |
|---|---|---|
| 8,114,345 B2 | 2/2012 | Dlugos, Jr. et al. |
| 8,882,792 B2 | 11/2014 | Dietz et al. |
| 8,915,842 B2 | 12/2014 | Weisenburgh, II et al. |
| 8,931,682 B2 | 1/2015 | Timm et al. |
| 8,945,098 B2 | 2/2015 | Seibold et al. |
| 2008/0081948 A1 | 4/2008 | Weisenburgh et al. |
| 2011/0118709 A1 | 5/2011 | Burbank |
| 2011/0118778 A1 | 5/2011 | Burbank |
| 2013/0282052 A1 | 10/2013 | Aranyi et al. |

(Continued)

OTHER PUBLICATIONS

Correlated Solutions, "Principle of Digital Image Correlation," 2013 (http://correlatedsolutions.com/digital-image-correlation/).

(Continued)

*Primary Examiner* — Karen Masih
(74) *Attorney, Agent, or Firm* — Mintz Levin Cohn Ferris Glovsky and Popeo, P.C.

(57) ABSTRACT

Various exemplary methods, systems, and devices for causing end effector motion with a robotic surgical system are provided. In general, a surgical tool can be configured to releasably and removably couple to a robotic surgical system. The robotic surgical system can include two motors configured to provide torque to the surgical tool to drive one single function of the surgical tool. In at least some embodiments, at least one of the two motors configured to cooperate with another motor to drive the single function of the surgical tool can be configured to drive a second function of the surgical tool.

16 Claims, 16 Drawing Sheets

(56) References Cited

U.S. PATENT DOCUMENTS

2014/0005718 A1     1/2014   Shelton, IV et al.
2017/0172672 A1*   6/2017   Bailey .................... A61B 34/30

OTHER PUBLICATIONS

U.S. Appl. No. 15/131,963 entitled "Method for Operating a Surgical Instrument" filed on Apr. 18, 2016.
U.S. Appl. No. 15/177,430 entitled "Surgical Instrument With User Adaptable Techniques" filed on Jun. 9, 2016.

* cited by examiner

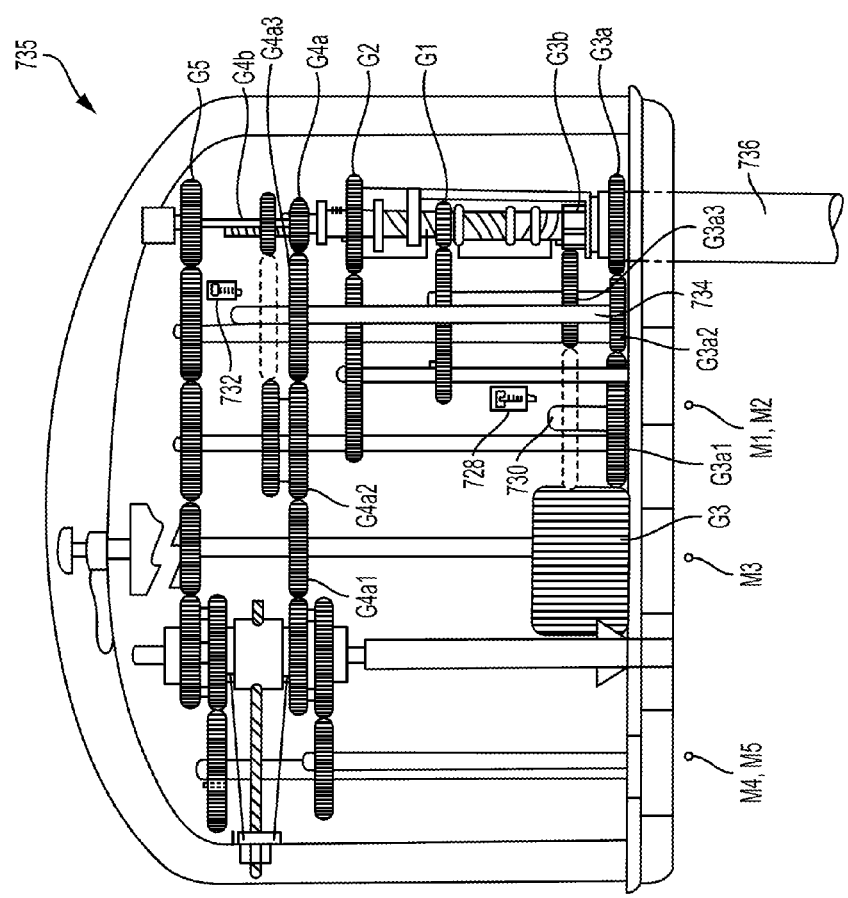

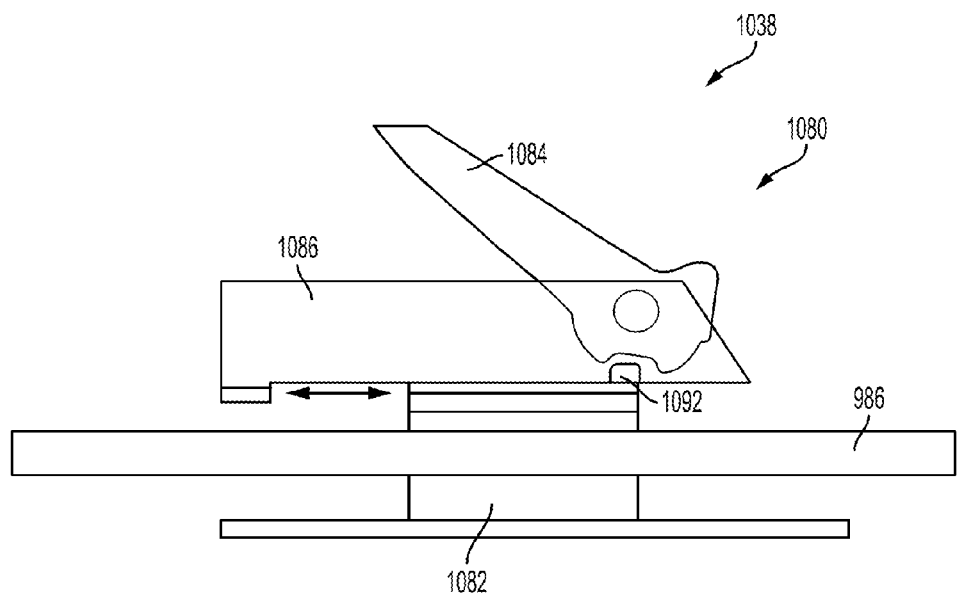
FIG. 8
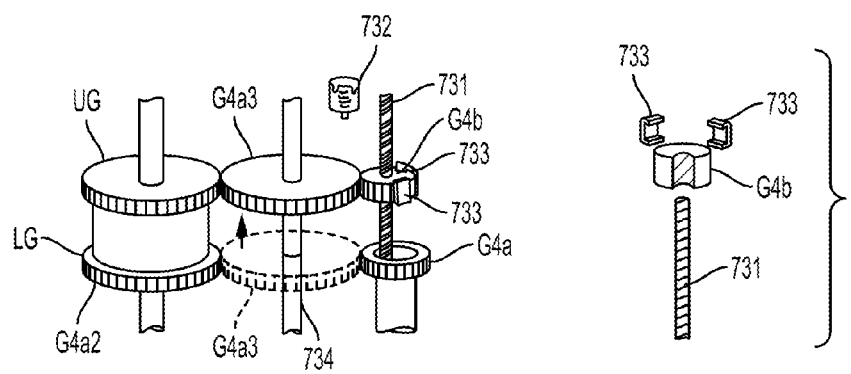
FIG. 9
FIG. 9A

METHODS, SYSTEMS, AND DEVICES FOR CAUSING END EFFECTOR MOTION WITH A ROBOTIC SURGICAL SYSTEM

FIELD

Methods and devices are provided for robotic surgery, and in particular for methods, systems, and devices for causing end effector motion with a robotic surgical system.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, methods, systems, and devices for causing end effector motion with a robotic surgical system are provided.

In one aspect, a surgical system is provided that in one embodiment includes a tool driver configured to releasably and replaceably engage with a surgical tool having an elongate shaft with an end effector at a distal end of the elongate shaft. The tool driver includes a plurality of motors and a plurality drive disks each configured to be simultaneously driven by at least one of the motors and thereby cause a single motion of the end effector.

The surgical system can vary in any number of ways. For example, the single motion can include any one of closing jaws of the end effector, articulating the end effector relative to the elongate shaft, translating a cutting element along the end effector, and rotating the end effector relative to the elongate shaft.

For another example, the tool driver can include a shaft having a plurality of gears attached thereto at different axial positions along a longitudinal length of the shaft, and the plurality of drive disks being simultaneously driven can be configured to cooperate to drive one of the gears and thereby cause the single motion of the end effector. In at least some embodiment, when the tool driver is releasably and replaceably engaged with the surgical tool, a longitudinal axis of the elongate shaft of the surgical tool can be substantially coaxial with a longitudinal axis of the shaft of the tool driver. In at least some embodiment, the driving of the one of the gears can cause the one of the gears to rotate about a longitudinal axis of the shaft of the tool driver, and/or each of the drive disks can include a gear.

For still another example, each of the drive disks can include a rotatable gear.

In another embodiment, a surgical system is provided that includes a surgical tool including an elongate shaft, an end effector at a distal end of the elongate shaft, and a plurality of actuation shafts operatively coupled to the end effector and extending along the elongate shaft. Each of the actuation shafts is configured to operate a function of the end effector such that the end effector has a plurality of functions. The surgical system also includes a tool driver configured to releasably and replaceably operatively engage the surgical tool. The tool driver includes a plurality of motors and a plurality of drive disks. Two of the drive disks are configured to be simultaneously driven by respective ones of the motors and thereby actuate one of the actuation shafts and cause one of the functions of the end effector.

The surgical system can have any number of variations. For example, the one of functions of the end effector can include any one of closing jaws of the end effector, articulating the end effector relative to the elongate shaft, translating a cutting element along the end effector, rotating the end effector relative to the elongate shaft, and rotating the elongate shaft and the end effector relative to a proximal housing of the surgical tool.

For another example, different combinations of two drive disks among the plurality of drive disks being simultaneously driven by respective ones of the motors can be configured to cause different ones of the functions of the end effector.

For yet another example, when the two drive disks are driven the drive disks can each be configured to rotate and thereby cause translation of the one of the actuation shafts to cause the one of the functions of the end effector. In at least some embodiments, the rotational movement of the drive disks can be transferred to the surgical tool as rotational motion, and the surgical tool can include an actuator configured to translate the rotational motion received from the tool driver to translational motion for the one of the actuation shafts. In at least some embodiments, the rotational movement of the drive disks can be transferred to the surgical tool as translational motion that causes the translation of the one of the actuation shafts.

For still another example, each of the drive disks can include a rotatable gear.

For another example, the plurality of drive disks can include three or more drive disks, and the plurality of motors can include three or more motors.

In another aspect, a surgical method is provided that in one embodiment includes actuating a plurality of motors of a tool driver of a robotic surgical system and thereby simultaneously drive more than one of a plurality of drive disks of the tool driver. The driving of the more than one of the plurality of drive disks causes performance of a single function of an end effector of a surgical tool among of plurality of possible functions of the end effector. The surgical tool includes a proximal housing releasably and replaceably coupled to the tool driver, and the surgical tool includes an elongate shaft extending distally from the proximal housing and having the end effector at a distal end thereof.

The surgical method can vary in any number of ways. For example, the single function of the end effector can include any one of closing jaws of the end effector, articulating the end effector relative to the elongate shaft, translating a cutting element along the end effector, rotating the end effector relative to the elongate shaft, and rotating the elongate shaft and the end effector relative to the proximal housing. For another example, the simultaneous driving of the more than one of the plurality of drive disks can cause a disk mounted on a drive shaft of the tool driver to rotate, and a longitudinal axis of the drive shaft can be substantially coaxial with the elongate shaft of the surgical tool.

BRIEF DESCRIPTION OF DRAWINGS

This invention will be more fully understood from the following detailed description taken in conjunction with the accompanying drawings, in which:

FIG. 5 is a partial cross-sectional side view of another embodiment of a puck and shaft of a surgical tool;

FIG. 8 is a partial side schematic view of one embodiment of an end effector having a knife actuation assembly;

FIG. 9 is a perspective view of engaged gears of the puck of FIG. 5 including a shiftable gear;

FIG. 9A is a an exploded partially cross-sectional view of one of the gears of FIG. 9 and a shaft on which the gear is movably attachable;

DETAILED DESCRIPTION

Figure 1:
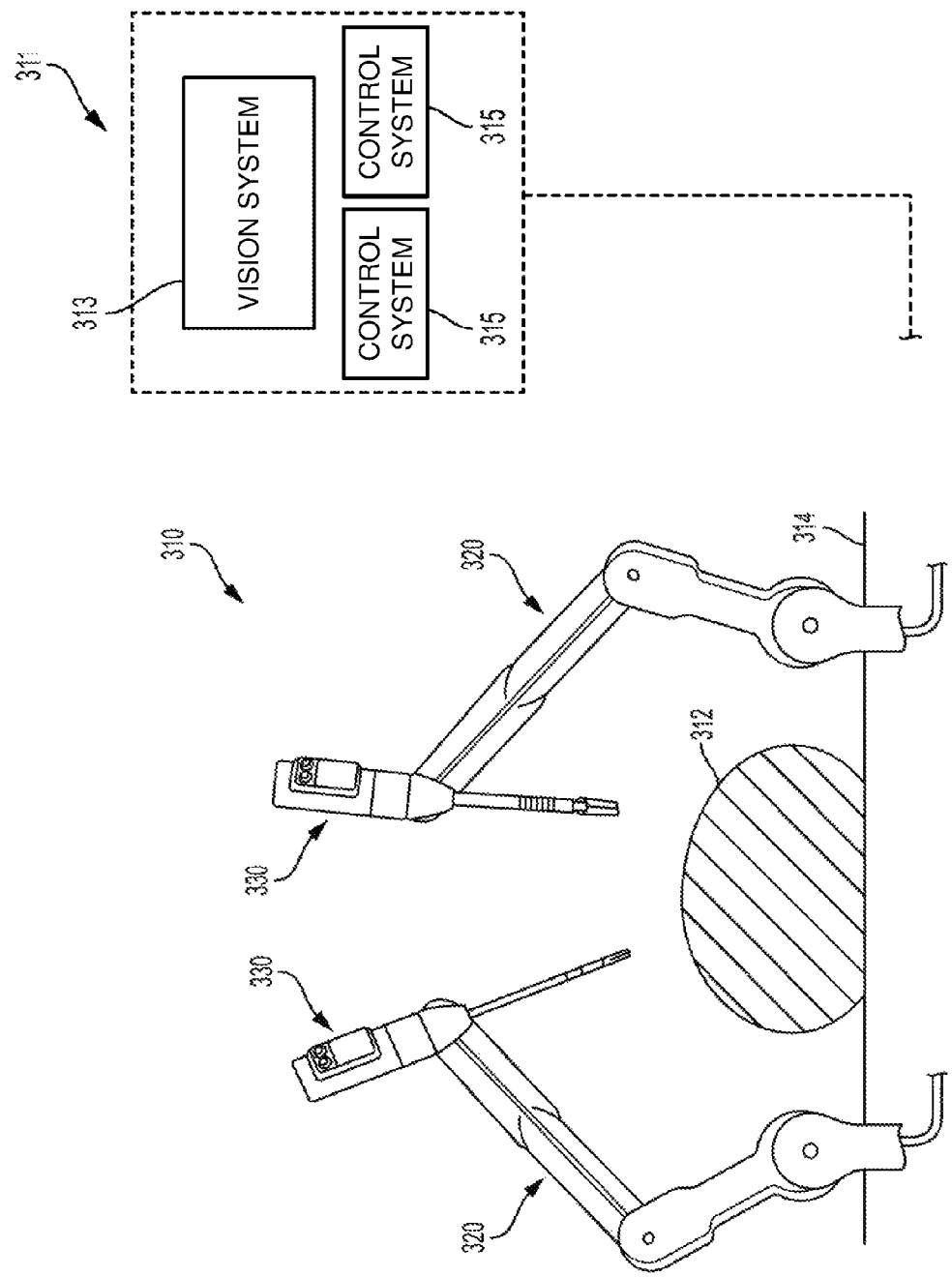
FIG. 1 is a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon.

Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for causing end effector motion with a robotic surgical system are provided. In general, a surgical tool can be configured to releasably and removably couple to a robotic surgical system. The robotic surgical system can include two motors configured to provide torque to the surgical tool to drive one single function of the surgical tool. One or both of the motors may thus be a less powerful motor, and hence be a less expensive motor and/or smaller motor, than a motor that would be needed to drive the single function on its own since the torque output of the two motors can combined to drive the single function of the surgical tool. For example, a function of closing an end effector of a surgical tool may require 400 lb. Each of the two motors can provide 200 lb to arrive at the required 400 lb to cause the end effector closure instead of a single motor providing all 400 lb.

In at least some embodiments, at least one of the two motors configured to cooperate with another motor to drive the single function of the surgical tool can be configured to drive a second function of the surgical tool. A single motor may thus be configured to drive two different functions of the surgical tool, which may result in a more cost efficient and/or space efficient system since one motor can cause multiple different functions to be performed instead of two motors being needed to cause those multiple functions. To allow the motor to drive two different functions, the motor can be configured to shift between a first mode, in which the motor drives the function in cooperation with another motor, and a second mode, in which the motor drives the second function. The motor may thus be selectively shifted to drive one function or another function as desired.

The robotic surgical system can include one or more motors in addition to the two motors configured to drive the single function. Each of the additional one or more motors can be configured to drive a function of the surgical tool that is different from each of the other functions of the surgical tool. The robotic surgical system may thus be configured to drive multiple different functions of the surgical tool, which may allow for more versatile use of the surgical tool in a body of a patient and/or allow two or more of the functions to be performed at the same time since the two or more functions can be simultaneously, respectively driven by two or more of the motors.

Functions of the surgical tool can include a function of an end effector of the surgical tool. Functions of the end effector can include, for example, a quick close of the end effector (e.g., closing jaws of the surgical tool at a first speed), a slower close of the end effector (e.g., closing jaws of the surgical tool at a second speed that is less than the first speed associated with quick close), articulation of the end effector relative to an elongate shaft of the surgical tool (e.g., angling the end effector relative to a longitudinal axis of the elongate shaft), rotation of the end effector relative to the elongate shaft (e.g., rotation of the end effector about a longitudinal axis thereof), and rotation of the end effector and the shaft as a unit about the longitudinal axis of the shaft.

Robotic Surgical Systems

The systems, devices, and methods disclosed herein can be implemented using a robotic surgical system.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and can be located adjacent to the patient, e.g., in the operating room, remote from the patient, e.g., in a separate control room, or the control system 315 can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
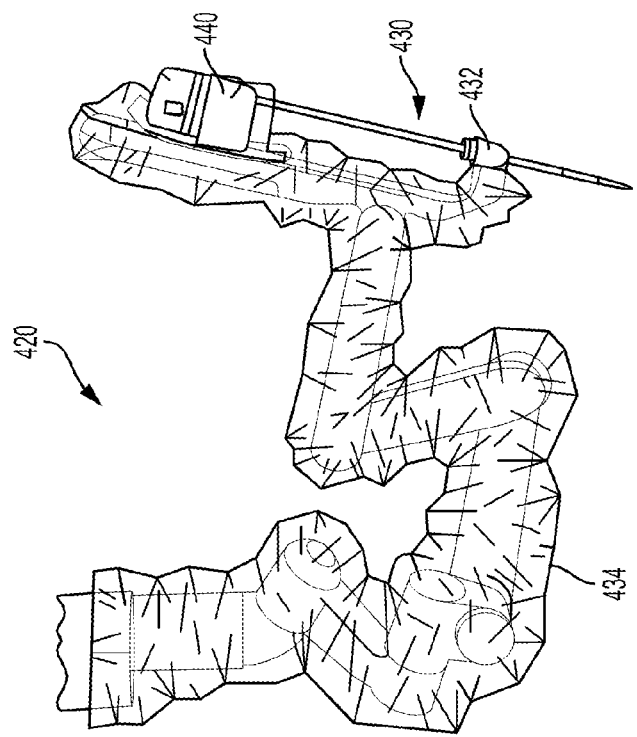
FIG. 2 is a perspective view of one embodiment of a robotic arm of a surgical robotic system with a surgical tool releasably and removably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430.

The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
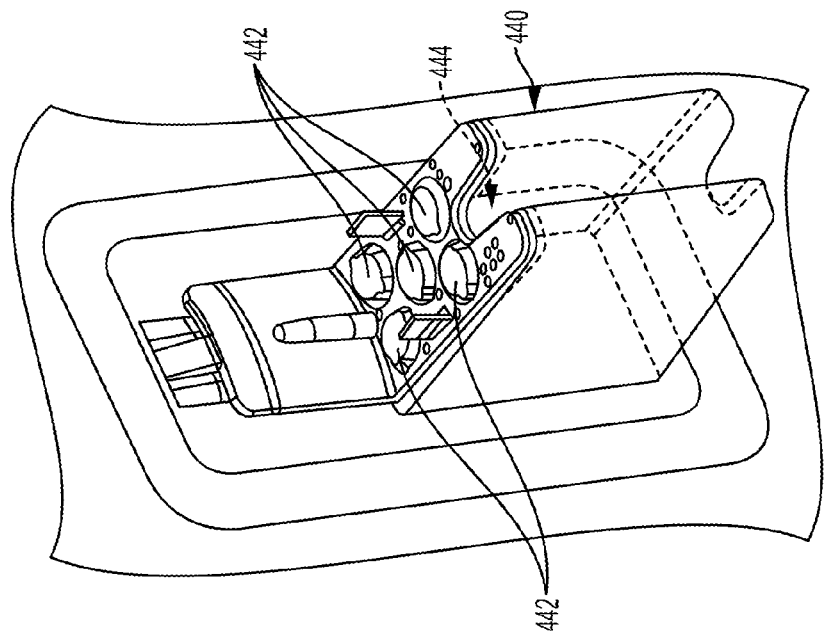
FIG. 3 is a perspective view of a tool driver of the robotic arm of FIG. 2.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
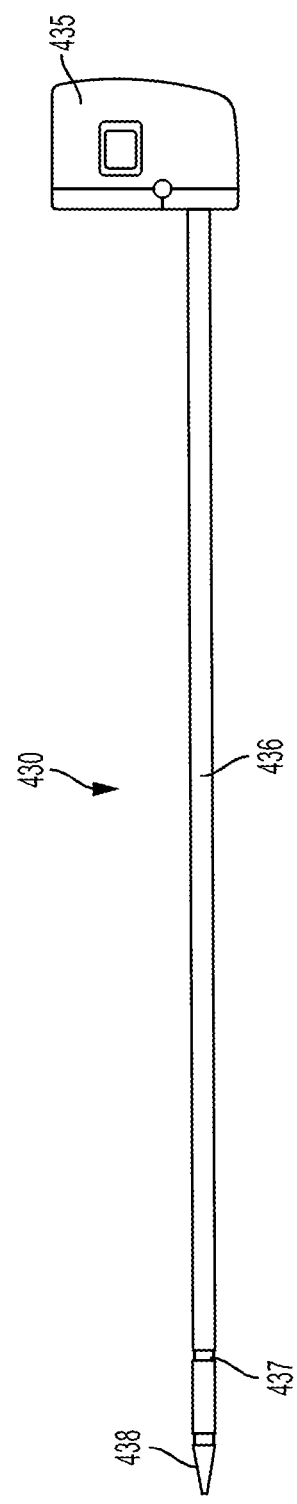
FIG. 4 is a side view of the surgical tool of FIG. 2 uncoupled from the robotic arm, the tool including a shaft extending from a puck at a proximal end and having an end effector located at a distal end of the shaft.

FIG. 4 illustrates the tool assembly 430 uncoupled from the robotic arm 420. The tool assembly 430 includes a housing or puck 435 coupled to a proximal end of the shaft 436 and an end effector 438 coupled to a distal end of the shaft 436. The puck 435 can include coupling features that assist with releasably coupling the puck 435 to the tool driver 440 of the robotic arm 420. The puck 435 can include gears and/or actuators that can be actuated by the one or more motors 442 in the driver 440, as will be described in greater detail below. The gears and/or actuators in the puck 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the puck 435, or it can be releasably coupled to the puck 435 such that the shaft 436 can be interchangeable with other shafts. This can allow a single puck 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applies, forceps, a needle driver, a cautery device, a cutting tool, a pair of jaws, an imaging device (e.g., an endoscope or ultrasound probe), or a combined device that includes a combination of two or more various tools.

FIG. 5 illustrates an embodiment of a puck 735 and a proximal end of a shaft 736 extending from the puck 735. As shown in FIG. 5, the puck 735 includes a plurality of actuation gears and gear shafts that can be either directly or indirectly controlled by any one of the motors 442 associated with the driver 440. For example, as shown in FIG. 5, the puck 735 is configured to couple to five motors at the locations indicated by reference numbers M1, M2, M3, M4, and M5. In this embodiment, the puck 735 includes first and second articulation gears G1, G2 that are coupled respectively to the first and second motors M1, M2 via a series of one or more additional gears and shafts. Actuation of the first and second motors M1, M2 will rotate the articulation gears UI, G2, which in turn cause linear movement of an articulation cable in a proximal or distal direction to thereby cause articulation of an end effector at a distal end of the shaft 736 in desired left and right directions. The puck 735 also includes a shaft rotation gear G3a that is coupled to the third motor M3 via a series of one or more additional gears and shafts. Actuation of the third motor M3 will thus rotate the shaft rotation gear G3a, thereby causing rotation of the shaft 736. The third motor M3 can also be configured to shift and to couple, via a series of one or more additional gears and shafts, to a head rotation gear G3b, which will cause rotation of the end effector relative to the shaft 736. The puck 735 further includes a firm close gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector. The puck 735 further includes a quick close gear G4b that can also couple to the fourth motor M4 via a series of one or more additional gears and shafts. When the fourth motor M4 is shifted into engagement with the quick close gear G4b, actuation of the fourth motor M4 will rotate the quick close gear G4b to cause linear translation of a quick close cable to quickly close the jaws of the end effector. Finally, the illustrated puck 735 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector, as will be discussed in more detail below.

Figures 6, 6A:
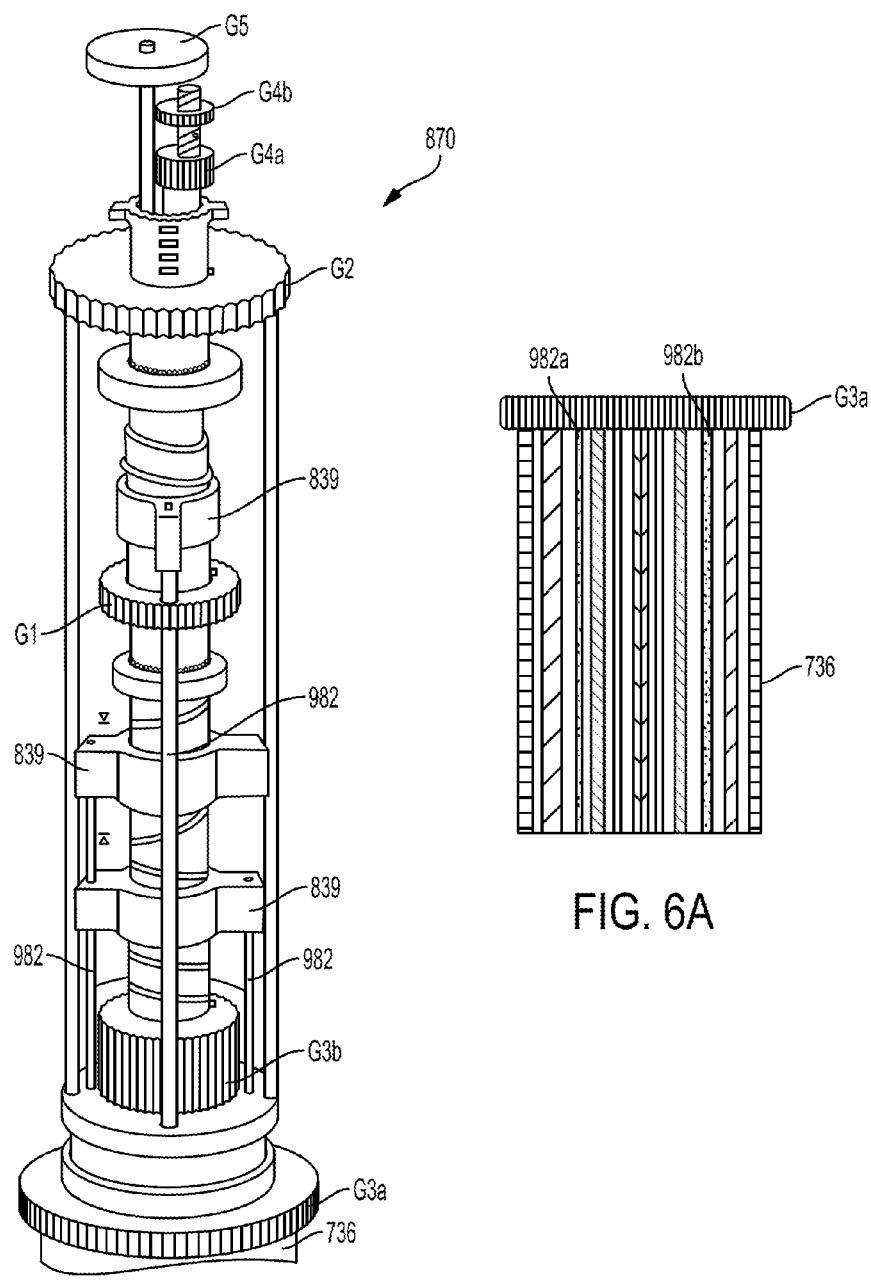
FIG. 6 is a perspective view of an actuation assembly of the puck of FIG. 5.
FIG. 6A is a side cross-sectional view of an elongate shaft extending distally from the actuation assembly of FIG. 6.
Figure 7:
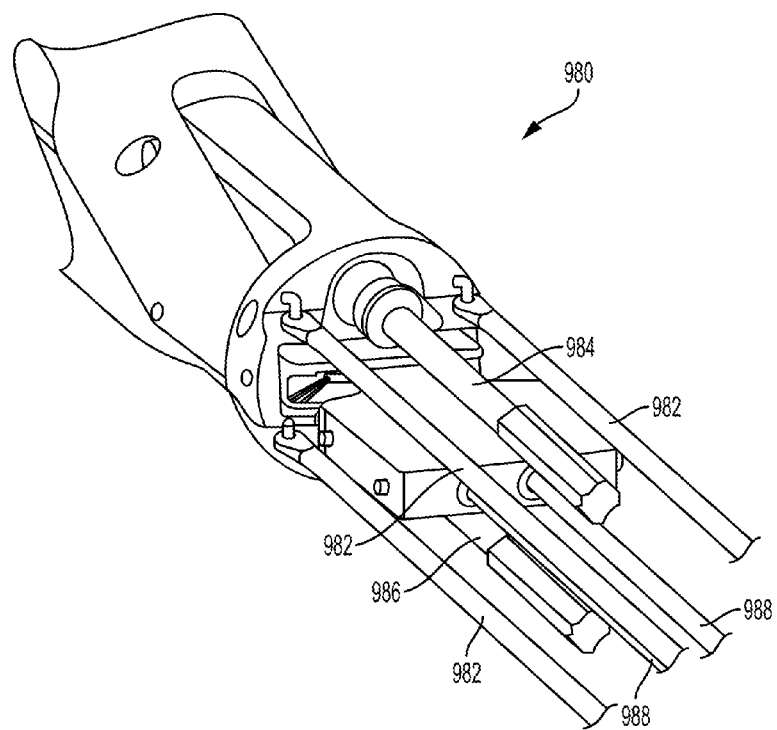
FIG. 7 is a perspective view of a wrist portion of the surgical tool of FIG. 4.

FIGS. 6-6A illustrate actuation assembly 870 components of the puck of FIG. 5. As shown and indicated above, each of the gears G1, G2, G3, G4, G5 is coupled to an actuation shaft that extends from the actuation assembly 870 and along the shaft 736 of the tool assembly, such as for controlling the movements of the end effector. FIG. 7 illustrates a distal end of the actuation shafts extending from a wrist 980 located just proximal of the end effector. The wrist 980 can allow for fine movements and angulation of the end effector relative to the proximal end of the shaft 736. As shown in FIG. 7, the wrist 980 includes four articulation cables 982 that are spaced around a perimeter of the wrist 980. When actuated (e.g., pushed, pulled, rotated), the articulation cables 982 will cause articulation of the end effector (e.g., movement up, down, left, right, and combinations thereof) relative to the proximal end of the shaft 436. The articulation cables 982 are connected to articulation couplers 839 shown in FIG. 6, that are driven proximally and distally when the articulation gears G1, G2 are actuated by the first and second motors M1, M2. The wrist 980 also includes an upper rotary driver 984 that when actuated can cause the pair of jaws of the end effector to firmly close. The upper rotary driver 984 is coupled to the firm close gear G4*a* shown in FIGS. 5 and 6 such that rotation of the firm close gear G4*a* by the motor M4 causes rotation of the rotary driver 984. The wrist 980 can also include a lower rotary driver 986 that when actuated can cause movement of a sled located at the end effector. The lower rotary driver 986 is coupled to the firing gear G5 shown in FIG. 6 and it likewise rotates in response to rotation of the firing gear G5. The illustrated wrist 980 further includes a linear pull cable 988 that is coupled to the quick close gear G4*b* shown in FIG. 6 and that moves linearly in a proximal direction to cause rapid close of the pair of jaws.

FIG. 8 illustrates a portion of an end effector 1038 having a knife actuation assembly 1080 that includes a drive member 1082, a knife 1084, a knife sled 1086, and a lead screw or rotary driver 986. The drive member 1082 includes internal threads that are threadably coupled with the rotary driver 986. Such coupling can allow drive member 1082 to move along the rotary driver 986 when the rotary driver 986 is rotated. As discussed above, the rotary driver 986 can be actuated at the wrist 980, as shown in FIG. 7, thereby causing rotation of the rotary driver 986 and linear movement of the knife sled 1086 along the rotary driver 986. The rotary driver 986 is coupled to the firing gear G5 shown in FIG. 6. The knife actuation assembly 1080 is configured to orient the knife 1084 in a cutting position when the drive member 1082 pushes the knife sled 1086 along the rotary driver 986 and to stow the knife 1084 when the drive member 1082 is moved proximally relative to the knife sled 1086. In operation, the rotary driver 986 is first rotated to advance the drive member 1082 distally along the rotary driver 986 thereby pushing the knife sled 1086 in the distal direction and angularly orienting the knife 1084 in the cutting position. At the end of the distal movement of the assembly 1080, the direction of rotation of the rotary driver 986 is reversed to retract the drive member 1082 proximally relative to the knife sled 1086, thereby causing the knife 1084 to rotate down into the stowed position, such as via interaction between an interface feature 1092 and the knife 1084.

As mentioned above, the fourth motor M4 of FIG. 5 is configured to be shifted between operative engagement with the firm close gear G4*a* to effect firm closure of the end effector and the quick close gear G4*b* to effect quick closure of the end effector. Spur gear G4*a*1 is rotatably coupled in a gear train with gears G4*a*2 and G4*a*3, terminating in the firm close gear G4*a*. The spur gear G4*a*1 can be rotatably coupled in another gear train with gears G4*a*2 and G4*a*3, terminating in the quick close gear G4*b*. Shiftable gear G4*a*3 is configured to shift the fourth motor M4 by moving between these two gear trains for the quick close gear G4*b* and the firm close gear G4*a*. In other words, movement of the shiftable gear G4*a*3 between a first position, in which the shiftable gear G4*a*3 is in the gear train for the firm close gear G4*a*, and a second position, in which the shiftable gear G4*a*3 is in the gear train for the quick close gear G4*b*, causes the fourth motor M4 to shift between driving firm close of the end effector (when the shiftable gear G4*a*3 is in the first position) and quick close of the end effector (when the shiftable gear G4*a*3 is in the second position). Thus, only one of the two gear trains for quick close and firm close can be active at one time for the fourth motor M4 to drive. The shiftable gear G4*a*3 is slidably mounted on a shaft 734 along which the shiftable gear G4*a*3 slides when moving between the first and second positions. FIG. 5 illustrates the shiftable gear G4*a*3 in solid line in the first position and the shiftable gear G4*a*3 in phantom (dotted line) in the second position. FIG. 9 illustrates the shiftable gear G4*a*3 in phantom in the first position and the shiftable gear G4*a*3 in solid line in the second position. The first position of the shiftable gear G4*a*3 is the default position of the shiftable gear G4*a*3. In this way, regular, faster closure of the end effector is the default mode of closure.

In both of the first and second positions, the shiftable gear G4*a*3 is engaged with spool gear G4*a*2, as shown in FIGS. 5 and 9. In the first position, the shiftable gear G4*a*3 is engaged with a lower gear LG of the spool gear G4*a*2. In the second position, the shiftable gear G4*a*3 is engaged with an upper gear UG of the spool gear G4*a*2.

As shown in FIGS. 5 and 9, the puck 435 includes an electromagnet 732 configured to be selectively actuated to shift the fourth motor M4 by moving the shiftable gear G4*a*3 between the first and second positions. The electromagnet 732 as shown is in the form of a solenoid. The electromagnet 732 is configured to be selectively actuated to generate a magnetic field within operative range of the shiftable gear G4*a*3. When the electromagnet 732 is not generating the magnetic field, the shiftable gear G4*a*3 is in the first position. When the electromagnet 732 is generating the magnetic field, the magnetic effect draws the shiftable gear G4*a*3 toward the electromagnet 732 to move the shiftable gear G4*a*3 from the first position to the second position, e.g., to cause the shiftable gear G4*a*3 to slide up the shaft 734. The shiftable gear G4*a*3 is thus made at least partially from a metal or other material configured to be affected by the magnetic field so as to allow the shiftable gear G4*a*3 to be drawn toward the electromagnet 732. Removal of the electromagnetic field allows the shiftable gear G4*a*3 to move from the second position to the first position, e.g., to slide down the shaft 734.

The electromagnet 732 can be actuated in any of a variety of ways to generate the magnetic field. For example, the electromagnet 732 can be configured to be operatively engaged with a current source in the tool driver (or elsewhere in the robotic surgical system of which the tool driver is a part) to which the puck 735 is releasably coupled, such as by a wire extending from the electromagnet 732 to a coupling on the puck 735 that engages a corresponding coupling on the tool driver. The robotic surgical system's current source can be activated to actuate the electromagnet 732. The robotic surgical system's current source can be activated in any number of ways, as will be appreciated by a person skilled in the art, such as by a user providing an input to an input tool of the robotic surgical system. For another example, the electromagnet 732 can be configured to be electrically activated to alternately push and pull an actuation rod that is operatively coupled to the shiftable gear G4*a*3. When the electromagnet 732 is inactive, the shiftable gear G4*a*3 is in the first position with the actuation rod located inside the electromagnet 732. When the electromagnet 732 is electrically activated, the actuation rod is pushed outward and advances the shiftable gear G4*a*3 to the second position.

One electromagnet 732 is used in this illustrated embodiment to move the shiftable gear G4*a*3, but more than one electromagnet can be used to move the shiftable gear G4*a*3 or any of the other shiftable gears described herein. Using more than one electromagnet can allow a great force to be generated, which may facilitate movement of larger gears and/or help ensure gear movement.

FIG. 9 and FIG. 9A illustrate gear supports 733 for the quick close gear G4*b*. The gear supports 733 are configured to maintain vertical position of the quick close gear G4*b* along a shaft 731 to which the quick close gear G4*b* is mounted while allowing rotation of the quick close gear G4*b* about the shaft 731. The quick close gear G4*b* being maintained in a vertical position may facilitate engagement of the quick close gear G4*b* with the shiftable gear G4*a*3 since the quick close gear G4*b* will be located in a predictable vertical location for engagement with the shiftable gear G4*a*3 when the shiftable gear G4*a*3 moves to its second position. Two gear supports 733 are shown, but another number of gear supports 733 may be used. Additionally, any of the non-shiftable gears described herein that are rotatably mounted on a shaft can be coupled to at least one gear support configured to maintain vertical position of the gear to help ensure engagement of the gear with the one or more other gears engaged therewith.

Figure 10:
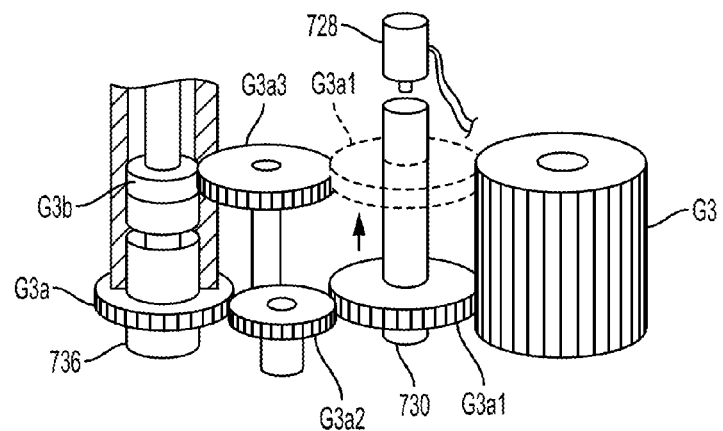
FIG. 10 is a perspective view of engaged gears of the puck of FIG. 5 including another shiftable gear.

As mentioned above, the third motor M3 is configured to be shifted between operative engagement with the shaft rotation gear G3*a* to effect causing rotation of the shaft 736 of the tool assembly and the head rotation gear G3*b* to effect rotation of the end effector relative to the shaft 736. As shown in FIGS. 5 and 10, a gear G3 is rotatably coupled in a gear train with gears G3*a*1 and G3*a*2, terminating in the shaft rotation gear G3*a*. The gear G3 can be rotatably coupled in another gear train with gears G3*a*1 and G3*a*3, terminating in the head rotation gear G3*b*. Shiftable gear Ci3*a*1 is configured to shift the third motor M3 by moving between these two gear trains for the shaft rotation gear G3*a* and the head rotation gear G3*b*. In other words, movement of the shiftable gear G3*a*1 between a first position, in which the shiftable gear G3*a*1 is in the gear train for the shaft rotation gear G3*a*, and a second position, in which the shiftable gear G3*a*1 is in the gear train for the head rotation gear G3*b*, causes the third motor M3 to shift between driving rotation of the end effector (when the shiftable gear G3*a*1 is in the first position) and rotation of the shaft 736 and the end effector (when the shiftable gear G3*a*1 is in the second position). Thus, only one of the two gear (rains for end effector rotation can be active at one time for the third motor M3 to drive. In both of the first and second positions, the shiftable gear G3*a*1 is engaged with gear G3, as shown in FIGS. 5 and 10. The shiftable gear G3*a*1 is slidably mounted on a shaft 730 along which the shiftable gear Wal slides when moving between the first and second positions. FIGS. 5 and 10 illustrate the shiftable gear G3*a*1 in solid line in the first position, and FIGS. 5 and 10 illustrate the shiftable gear G3*a*1 in phantom (dotted line) in the second position. The first position of the shiftable gear G3*a*1 is the default position of the shiftable gear G3*a*1. In this way, rotation of the end effector relative to the shaft 736 is the default mode of end effector rotation.

As shown in FIGS. 5 and 10, the puck 735 includes an electromagnet 728 configured to be selectively actuated to shift the third motor M3 by moving the shiftable gear G3*a*1 between the first and second positions. The electromagnet 735 as shown is in the form of a solenoid and can be configured to be activated and deactivated to move the shiftable gear G3*a*1 similar to the electromagnet 732 discussed above that can be activated and deactivated to move the shiftable gear G4*a*3. The shiftable gear G3*a*1 is thus made at least partially from a metal or other material configured to be affected by the magnetic field so as to allow the shiftable gear G3*a*1 to be drawn toward the electromagnet 728.

Figures 11, 12:
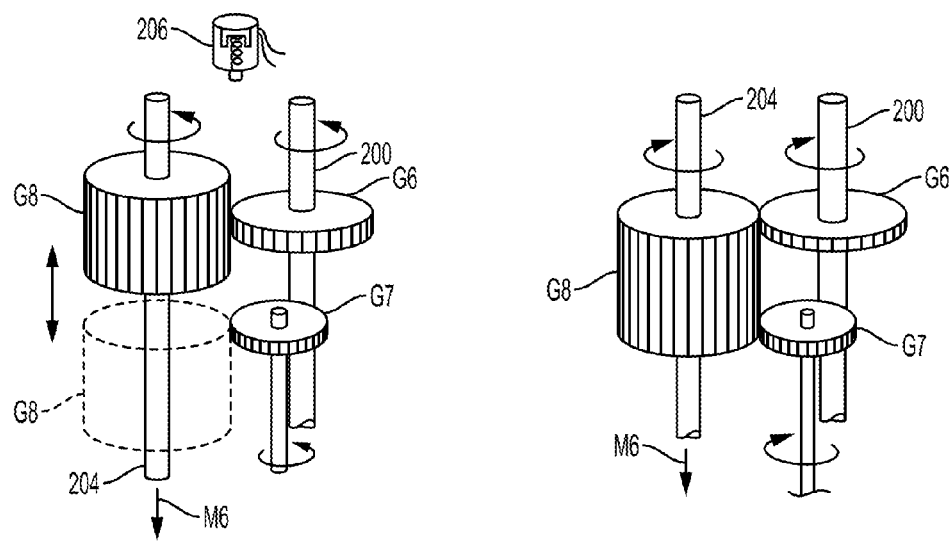
FIG. 11 is a perspective view of another embodiment of engaged gears including a shiftable gear.
FIG. 12 is a perspective view of the engaged gears of FIG. 12 with the shiftable gear in a third position.

FIGS. 11 and 12 illustrate another embodiment of components that can be included in a puck (e.g., the puck 435 of FIG. 4) to shift a motor M6 between operative engagement with gears G6, G7 each associated with a different function of a surgical tool (e.g., the tool 430 of FIG. 4) that can be releasably and removably coupled to the puck. Only one motor M6 and associated function gears G6, G7 are illustrated, but as discussed above, the puck can include one or more additional motors and one or more additional function gears. The firing gear G6 is mounted on a shaft 200 and is configured to be selectively engaged with a shiftable gear G8 configured to be rotated in response to actuation of the motor M6. The firing gear G6 can be configured and used similar to the firing gear G5 of FIG. 5, e.g., actuation of the motor M6 can rotate the firing gear GG, thereby driving a lead screw linearly to advance a sled through an end effector of the surgical tool. The firm close gear G7 is mounted on a shaft 202 and is configured to be selectively engaged with the shiftable gear G8. The firm close gear G7 can be configured and used similar to the firm close gear G4*a* of FIG. 5, e.g., actuation of the motor M6 can rotate the firm close gear G7, thereby effecting firm closure of the end effector. Although the gear G8 is shown attached to a shaft 204 that extends to the motor M6, the gear G8 can instead be part of a gear train that extends to the motor G6, similar to gear trains discussed above with respect to FIG. 5.

As shown in FIG. 11, the shiftable gear G8 is configured to shift the motor M6 by moving between a first position, in which the shiftable; gear G8 is engaged with the firm close gear G7, and a second position, in which the shiftable gear G8 is engaged with the firing gear G6, causes the motor M6 to shift between driving firm close of the end effector (when the shiftable gear G8 is in the first position) and firing of the end effector (when the shiftable gear G8 is in the second position). The shiftable gear G8 is also configured to move between a third position and either of the first and second positions. As shown in FIG. 12, the shiftable gear G8 in the third position is engaged with both of the firm close gear G7 and the firing gear G6. Thus, with the shiftable gear G8 in the third position, the motor M6 can be actuated to simultaneously rotate the firm close gear G7 and the firing gear G6. Such simultaneous actuation may allow, at the same time, the end effector to open and the sled to retract. This may help speed performance of a surgical procedure and/or allow faster disengagement of the end effector from tissue. The shiftable gear G8 is slidably mounted on the shaft 204 along which the shiftable gear G8 slides when moving between the first, second, and third positions. FIG. 11 illustrates the shiftable gear G8 in solid line in the second position and the shiftable gear G8 in phantom (dotted line) in the first position. FIG. 12 illustrates the shiftable gear G8 in the third position. The first position of the shiftable gear G8 is the default position of the shiftable gear G8. Since closing of the end effector is the first of closure and firing to occur, this closure can occur without the motor M6 first having to be shifted.

As shown in FIG. 11, the puck includes an electromagnet 206 configured to be selectively actuated to shift the motor M6 by moving the shiftable gear G8 between the first, second, and third positions. The electromagnet 206 as shown is in the form of a solenoid and can be configured to be activated and deactivated to move the shiftable gear G8 similar to the electromagnet 732 discussed above that can be activated and deactivated to move the shiftable gear G4*a*3. The shiftable gear G8 is thus made at least partially from a metal or other material configured to be affected by the magnetic field so as to allow the shiftable gear G8 to be drawn toward the electromagnet 206.

Figure 13:
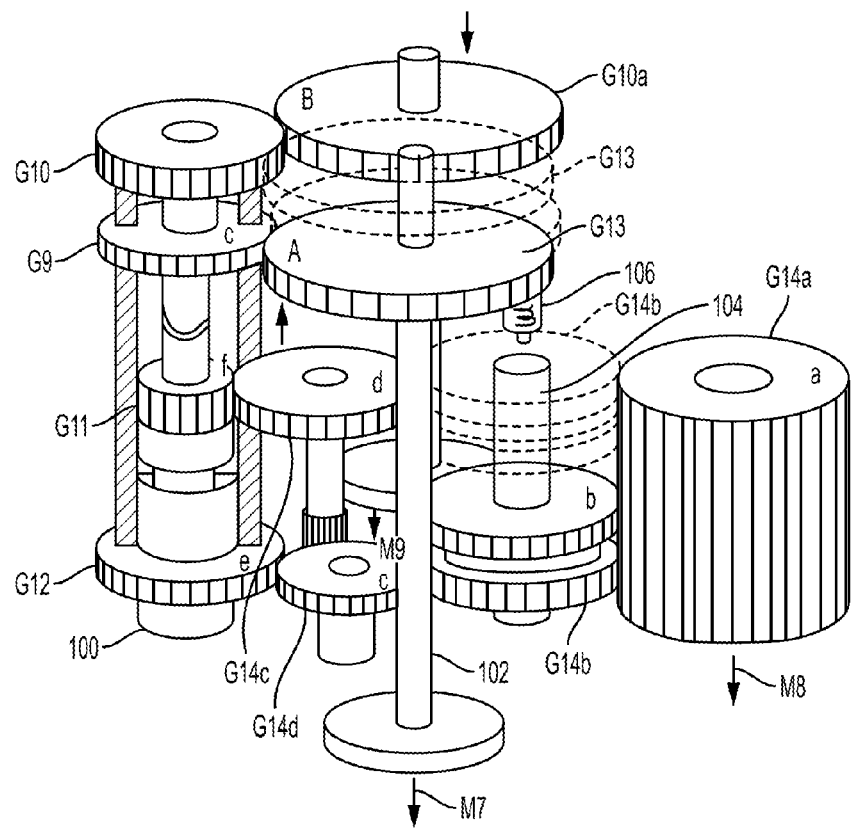
FIG. 13 is a perspective view of another embodiment of engaged gears including two shiftable gears.

FIG. 13 illustrates another embodiment of components that can be included in a puck (e.g., the puck 435 of FIG. 4) to shift each of two motors M7, M8 between operative engagement with gears each associated with a different function of a surgical tool (e.g., the tool 430 of FIG. 4) that can be releasably and removably coupled to the puck. FIG. 13 also illustrates an elongate shaft 100 of the surgical tool. Only three motors M7, M8, M9 and their variously associated function gears G9, G10, G11, G12 are illustrated, but as discussed above, the puck can include one or more additional motors and one or more additional function gears.

The puck includes the first and second articulation gears G9, G10 that can be configured and used similar to the first and second articulation gears G1, G2 of FIG. 5. The second actuation gear G10 is operatively coupled to the motor M9. Actuation of the motor M9 will rotate a gear G10a and thereby rotate the second actuation gear G10 to cause linear movement of an articulation cable of the surgical tool in a proximal or distal direction to thereby cause articulation of an end effector at a distal end of the shaft 100 in a desired left or right direction. The first actuation gear G9 is operatively coupled to the motor M7. Actuation of the motor M7 will rotate a shiftable gear G13 (when engaged with the first actuation gear G9, as discussed further below) and thereby rotate the first actuation gear G9 to cause linear movement of an articulation cable of the surgical tool in a proximal or distal direction to thereby cause articulation of an end effector at a distal end of the shaft 100 in a desired left or right direction.

Figure 14:
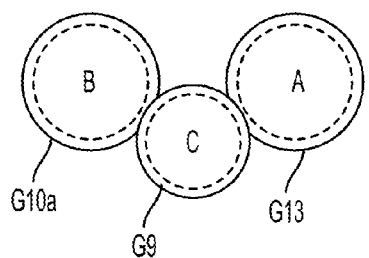
FIG. 14 is a top schematic view of one of the shiftable gears of FIG. 13 in a second position.

The shiftable gear G13 is configured to shift the motor M7 by moving between a first position, in which the shiftable gear G13 is engaged with the first actuation gear G9, and a second position, in which the shiftable gear G13 is engaged with the second actuation gear G10, causes the motor M7 to shift between driving different desired articulations of the end effector. FIG. 13 illustrates the shiftable gear G13 in solid line in the first position and the shiftable gear G13 in phantom (dotted line) in the second position. FIG. 14 illustrates the shiftable gear G13 in the second position. The first position of the shiftable gear G13 is the default position of the shiftable gear G13. When the shiftable gear G13 is in the second position, both the shiftable gear G13 driven by the motor M7 and the gear G10a driven by the motor M9 will drive the second articulation gear G10. The second articulation gear G10 can thus be driven with a first amount of torque when only the motor M9 drives it (e.g., when the shiftable gear G13 is in the first position) or driven with a second, greater amount of torque when the two motors M7, M9 cooperate to drive it (e.g., when the shiftable gear G13 is in the second position). The motor M7 may thus be configured to provide backup torque for articulation effected by the second articulation gear G10, which may allow for a smaller motor M9, and hence a less expensive motor and/or smaller motor, to be used in the puck since the motor M7 may provide more torque if needed by shifting the shiftable gear G13 to be in engagement with the second articulation gear G10.

The shiftable gear G13 is slidably mounted on a shaft 102 along which the shiftable gear G13 slides when moving between the first and second positions. The puck can include an electromagnet (not shown) configured to be selectively actuated to shift the motor M7 by moving the shiftable gear G13 between the first and second positions. The shiftable gear G13 can thus be made at least partially from a metal or other material configured to allow the shiftable gear G13 to be drawn toward the electromagnet.

Figure 15:
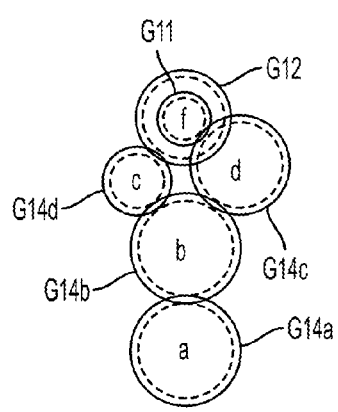
FIG. 15 is a top schematic view of another one of the shiftable gears of FIG. 13 in a second position.

The puck includes the head rotation gear G11, which can be configured and used similar to the head rotation gear G3b of FIG. 5. The head rotation gear G11 can be coupled to the motor M8 via a gear train that includes a gear G14a, a shiftable spool gear G14b, and a gear G14c. The puck also includes the shaft rotation gear G12, which can be configured and used similar to the head rotation gear G3a of FIG. 5. The shaft rotation gear G12 can be coupled to the motor M8 via a gear train that includes the gear G14a, the shiftable spool gear G14b, and a gear G14d. The motor M8 is configured to shift to selectively couple to either the head rotation gear G11, to allow for end effector rotation relative to the elongate shaft and the puck, or the shaft rotation gear G12, to allow for end effector and elongate shaft rotation relative to the puck. The shiftable spool gear G14b is configured to shift the motor M8 by moving between a first position, in which the shiftable spool gear G14b is operatively coupled with the shaft rotation gear G12, and a second position, in which the shiftable spool gear G14b is engaged with the head rotation gear G11, causes the motor M8 to shift between driving different desired rotations of the surgical tool. FIG. 13 illustrates the shiftable spool gear G14b in solid line in the first position and the shiftable spool gear G14b in phantom (dotted line) in the second position. FIG. 15 illustrates the shiftable spool gear G14b in the second position. The first position of the shiftable spool gear G14b is the default position of the shiftable spool gear G14b.

The shiftable spool gear G14b is slidably mounted on a shaft 104 along which the shiftable spool gear G14b slides when moving between the first and second positions. The puck includes an electromagnet 106 configured to be selectively actuated to shift the motor M8 by moving the shiftable spool gear G14b between the first and second positions. The shiftable spool gear G14b is thus made at least partially from a metal or other material configured to allow the shiftable spool gear G14b to be drawn toward the electromagnet 106.

Although the puck of FIG. 13 includes two shiftable gears G13, G14b, a puck can include only one or the other of the shiftable gears G13, G14b. In other words, in other embodiments, only one of the motors M7, M8 may be shiftable.

Figure 16:
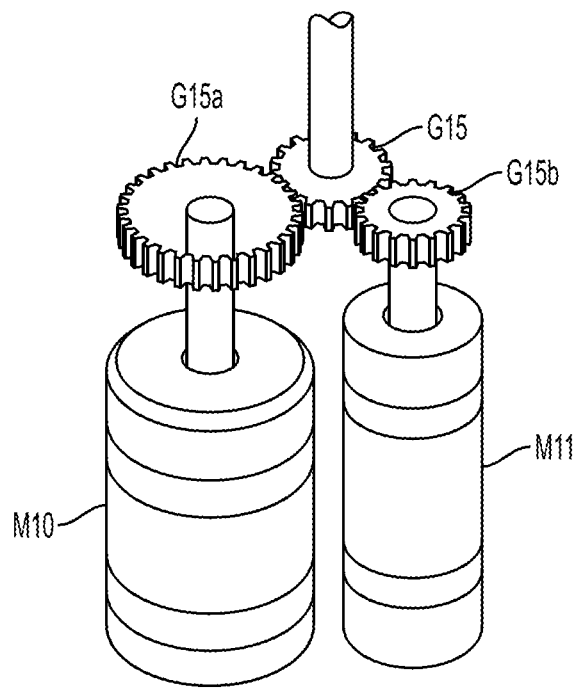
FIG. 16 is a perspective view of one embodiment of two motors of a tool driver operatively coupled to a gear of a puck.

FIG. 16 illustrates another embodiment of two motors M10, M11 of a tool driver of a robotic surgical system configured to cooperate to drive a function gear G15 in a puck of a surgical tool to effect a function of the surgical tool's end effector. This setup is similar to the two motors M7, M9 cooperating to drive the second articulation gear G10 of FIG. 13 to effect articulation of the end effector. One motor M10 is a high torque motor (e.g., a 12 Volt motor) configured to provide a relatively high torque to the surgical tool to cause rotation of the function gear G15. The other motor M11 is a high speed motor (e.g., a 48 Volt motor) configured to rotate at a relatively high speed to provide torque to the surgical tool to cause rotation of the function gear G15 in cooperation with the motor M10. The motors M10, M11 having different characteristics (e.g., one high torque and one high speed) may allow for versatile actuation of the function of the end effector associated with the function gear G15 (e.g., end effector rotation, end effector and elongate shaft rotation, firing, etc.) since a maximum amount of torque that can be provided to the tool is greater than would be available if only one of the motors M10, M11 was used to drive the function gear G15.

In the illustrated embodiment of FIG. 16, gears G15a, G15b coupled to the motors M10, M11, respectively, are always engaged with the function gear G15. In other embodiments, one of the gears G15a, G15b can be movable to shift their respective one of the motors M10, M11, as discussed above.

Figure 17:
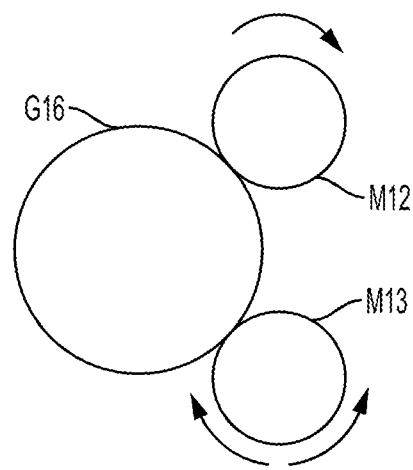
FIG. 17 is a top schematic view of another embodiment of two motors of a tool driver operatively coupled to a gear of a puck.
Figure 18:
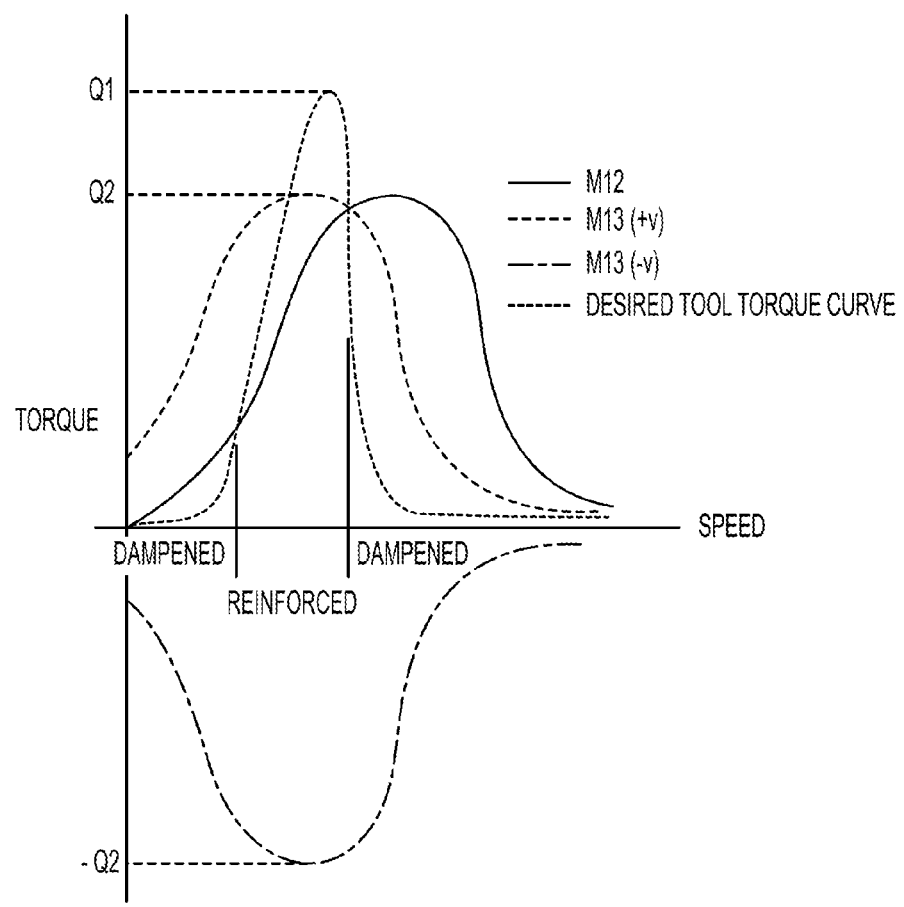
FIG. 18 is a graph showing a performance of the motors of FIG. 17.

FIG. 17 schematically illustrates one embodiment of two motors M12, M13 of a tool driver of a robotic surgical system configured to cooperate to drive a function gear G16 in a puck of a surgical tool to effect a function of the surgical tool's end effector. FIG. 18 illustrates performance of the motors M12, M13. In this illustrated embodiment, one motor M12 has a higher speed than the other motor M13, e.g., 10,000 rpm for the motor M12 and 8,000 rpm for the motor M13. As shown in FIG. 18, when both of the motors M12, M13 provide torque to drive the function gear G16, a resulting desired tool torque curve has a higher peak than that achieved when only one of the motors M12, M13 provides torque. In other words, a maximum amount of torque Q1 that can be provided to drive the function gear G16 with both of the motors M12, M13 is greater than a maximum amount of torque Q2 that can be provided by either one of the motors M12, M13 alone.

Figure 19:
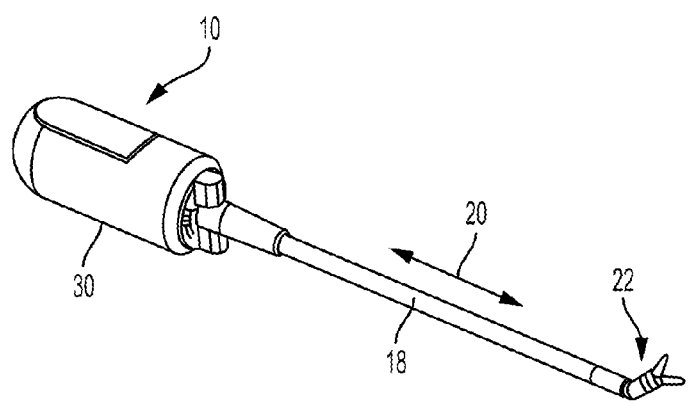
FIG. 19 is a perspective view of another embodiment of a surgical tool.
Figures 20, 21:
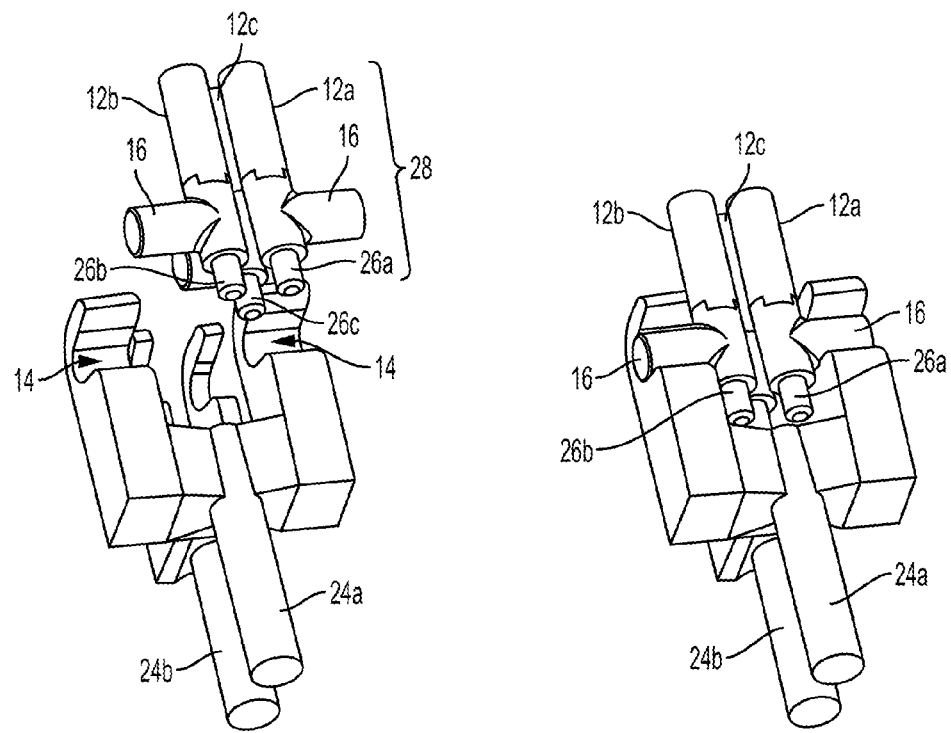
FIG. 20 is an exploded view of a portion of the surgical tool of FIG. 19 and a tool driver.
FIG. 21 is a perspective view of the portion of the surgical tool of FIG. 20 coupled to the tool driver.

FIGS. 19-21 illustrate another embodiment of two motors of a tool driver 28 of a robotic surgical system configured to cooperate to drive a function in a puck 30 of a surgical tool 10 to effect a function of an end effector 22 at a distal end of an elongate shaft 18. Each of the first and second motors are operatively coupled to first and second actuation shafts 12a, 12b, respectively. The tool driver 28 also includes a third motor operatively coupled to a third actuation shaft 12c.

When the surgical tool 10 is releasably and removably coupled to the tool driver 28 (e.g., mating elements 16 of the tool driver 28 are seated in corresponding mating features 14 of the puck 30), as illustrated in FIGS. 19 and 21, the first and second motors, via the first and second actuation shafts 12a, 12b, are configured to drive a first actuation shaft 24a of the surgical tool 10 to drive a first function of the end effector 22, and the third motor, via the third actuation shaft 12c, is configured to drive a third actuation shaft 24b of the surgical tool 10 to drive a second function of the end effector 22 that is different from the first function of the end effector 22. Thus, two motors (the first and second motors) are configured to drive a single function of the end effector 22 via the first actuation shaft 24a of the tool 10, which may provide any of a variety of benefits, as discussed herein. In this illustrated embodiment, the actuation shafts 12a, 12b, 12c of the tool driver 28 are configured to linearly translate to cause linear translation of their respective actuation shafts 24a, 24b of the tool 10. This linear translation is shown by arrow 20 in FIG. 19.

Various features that can be included in and various functionalities of the surgical tool 10 of FIG. 19 are further described in U.S. Pat. No. 8,945,098 entitled "Surgical Manipulation Instrument" filed on Nov. 30, 2010, which is hereby incorporated by reference in its entirety.

Figure 22:
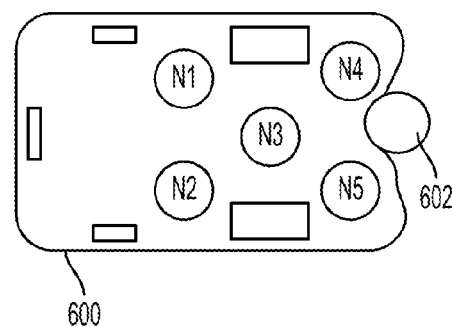
FIG. 22 is a side view of another embodiment of a puck and elongate shaft of a surgical tool.
Figure 23:
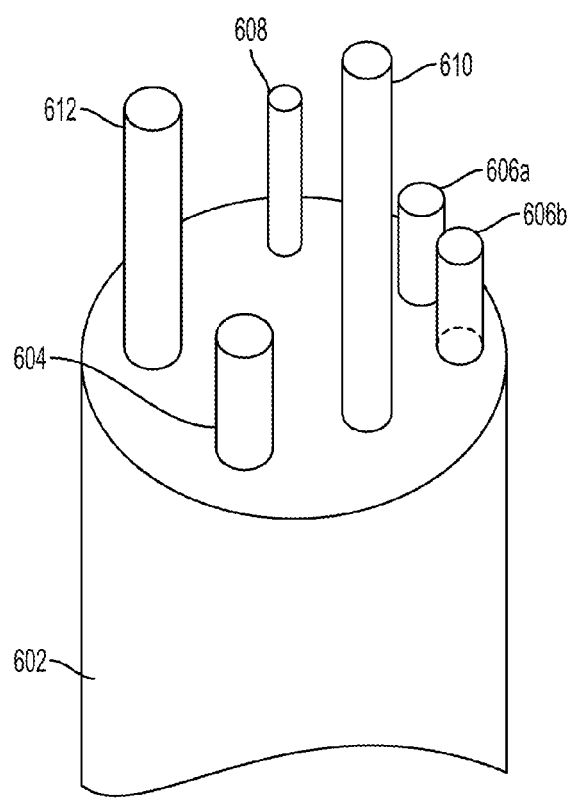
FIG. 23 is a perspective view of the elongate shaft of FIG. 22 and actuation shafts extending along the elongate shaft.

FIGS. 22 and 23 illustrate another embodiment of a puck 600 having an elongate shaft 602 extending distally therefrom. The puck 600 is configured to couple to five motors at the locations indicated by reference numbers N1, N2, N3, N4, and N5. Each of the motors can be configured to drive a function of an end effector at a distal end of the elongate shaft 602, either alone or in cooperation with one of the other motors, as described herein. The functions of the d effector are effected via actuation elements that extend along the elongate shaft 602. The actuation elements include an articulation rod 604 configured to be actuated to cause up/down articulation of the end effector, first and second articulation cables 606a, 606b configured to be actuated to cause left/right articulation of the end effector, an actuation shaft 608 configured to be actuated to cause quick closure of the end effector, an actuation shaft 610 configured to be actuated to cause firm closure of the end effector, and an actuation shaft 612 configured to cause firing of the end effector.

Figure 24:
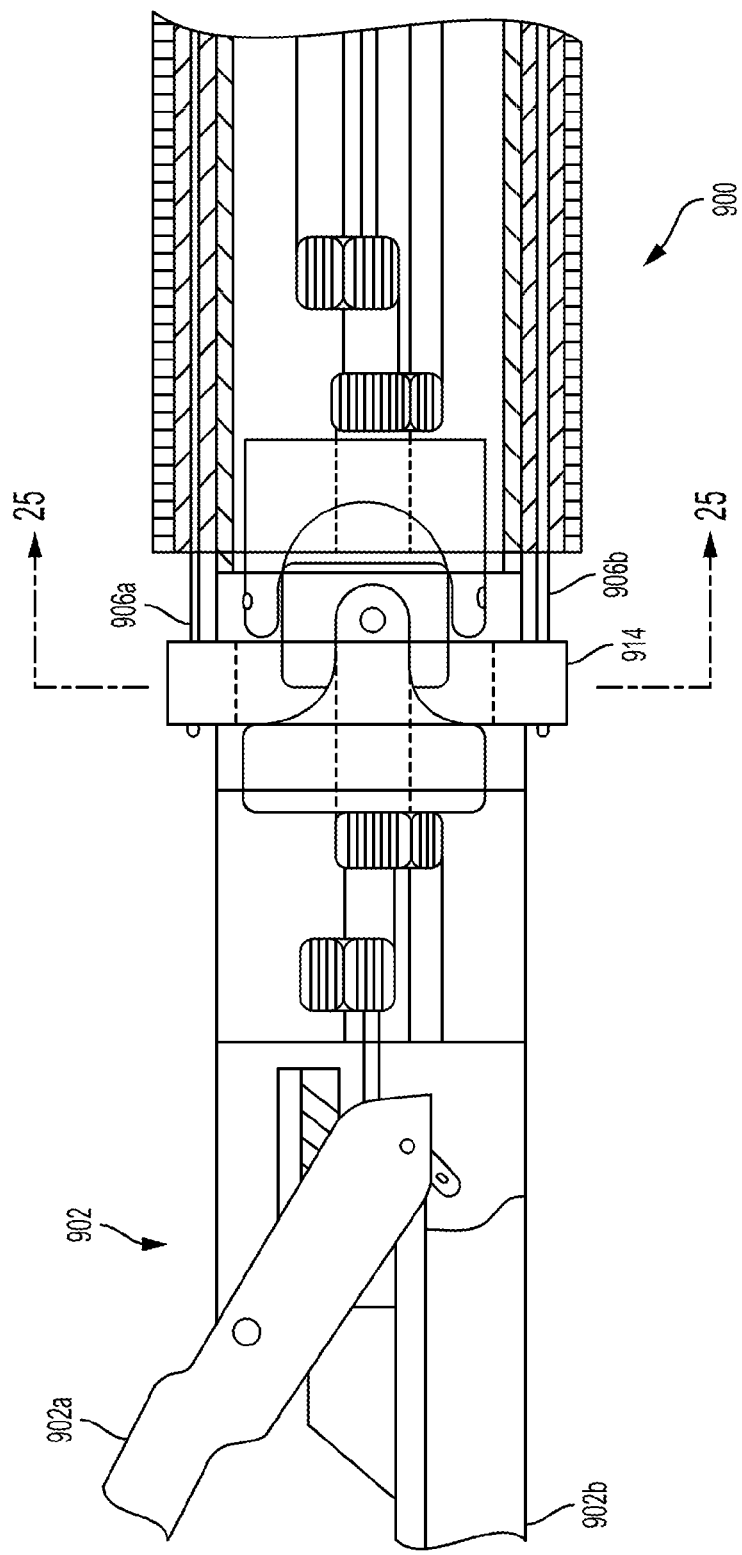
FIG. 24 is a side cross-sectional view of a portion of another embodiment of an elongate shaft and end effector of a surgical tool.
Figure 25:
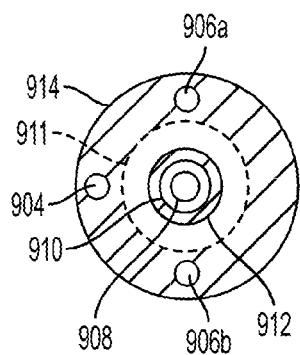
FIG. 25 is a cross-sectional view of the surgical tool of FIG. 24.

FIGS. 24 and 25 illustrate a portion of another embodiment of a surgical tool configured to releasably and replaceably couple to a tool driver of a robotic surgical system and including an elongate shaft 900 having an end effector 902 at a distal end thereof. Functions of the end effector 902 are effected via actuation elements that extend along the elongate shaft 602. The actuation elements include an articulation rod 904 configured to be actuated to cause up/down articulation of the end effector 902, first and second articulation cables 906a, 906b configured to be actuated to cause left/right articulation of the end effector 902, an actuation shaft 908 configured to be actuated to cause quick closure of the end effector 902 (e.g., quick closure of jaws 902a, 902b of the end effector 902), an actuation shaft 910 configured to be actuated to cause firm closure of the end effector 902 (e.g., firm closure of the jaws 902a, 902b), a rotation shaft 911 configured to cause rotation of the end effector 902, and an actuation shaft 912 configured to cause firing of the end effector 902. The surgical tool includes a hub 914 at a distal end of the elongate shaft 900 that has distal ends of the first and second articulation cables 906a, 906h attached thereto. The hub 914 is pivotably coupled to the elongate shaft 900 at a pivot point 916 that allows pivoting movement of the hub 914 to effect the left/right articulation of the end effector 902.

Terminology

Figure 26:
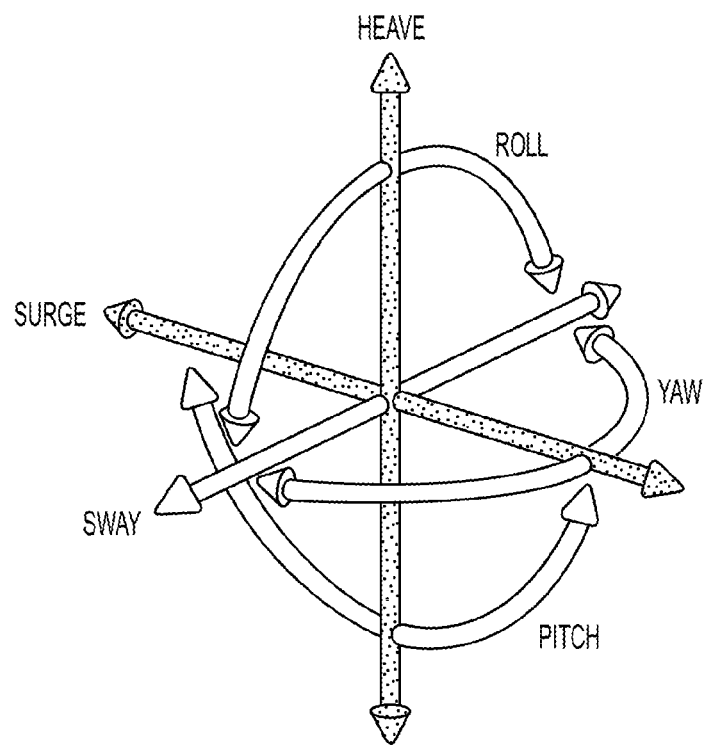
FIG. 26 is a graphical representation of terminology associated with six degrees of freedom.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 26, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 27:
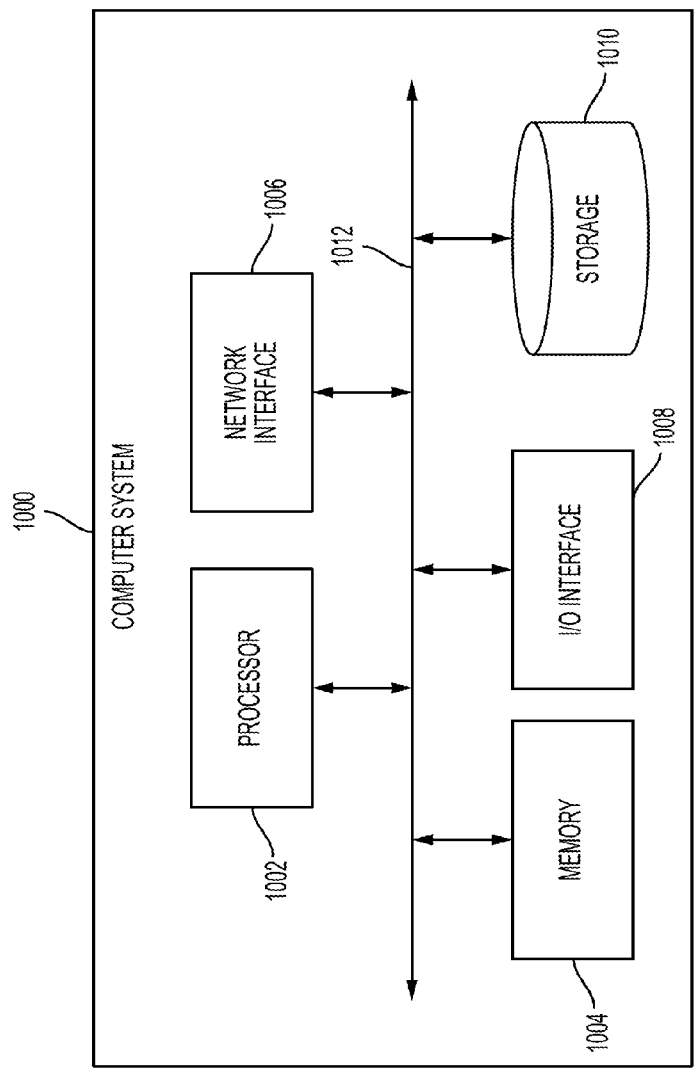
FIG. 27 is a schematic view of one embodiment of a computer system.

FIG. 27 illustrates one exemplary embodiment of a computer system 1000. As shown, the computer system 1000 includes one or more processors 1002 which can control the operation of the computer system 1000. "Processors" are also referred to herein as "controllers." The processor(s) 1002 can include any type of microprocessor or central processing unit (CPU), including programmable general-purpose or special-purpose microprocessors and/or any one of a variety of proprietary or commercially available single or multi-processor systems. The computer system 1000 can also include one or more memories 1004, which can provide temporary storage for code to be executed by the processor(s) 1002 or for data acquired from one or more users, storage devices, and/or databases. The memory 1004 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1000 can be coupled to a bus system 1012. The illustrated bus system 1012 is an abstraction that represents any one or more separate physical busses, communication lines/interfaces, and/or multi-drop or point-to-point connections, connected by appropriate bridges, adapters, and/or controllers. The computer system 1000 can also include one or more network interface(s) 1006, one or more input/output (IO) interface(s) 1008, and one or more storage device(s) 1010.

The network interface(s) 1006 can enable the computer system 1000 to communicate with remote devices, e.g., other computer systems, over a network, and can be, for non-limiting example, remote desktop connection interfaces, Ethernet adapters, and/or other local area network (LAN) adapters. The IO interface(s) 1008 can include one or more interface components to connect the computer system 1000 with other electronic equipment. For non-limiting example, the IO interface(s) 1008 can include high speed data ports, such as universal serial bus (USB) ports, 1394 ports, Wi-Fi, Bluetooth, etc. Additionally, the computer system 1000 can be accessible to a human user, and thus the IO interface(s) 1008 can include displays, speakers, keyboards, pointing devices, and/or various other video, audio, or alphanumeric interfaces. The storage device(s) 1010 can include any conventional medium for storing data in a non-volatile and/or non-transient manner. The storage device(s) 1010 can thus hold data and/or instructions in a persistent state, i.e., the value(s) are retained despite interruption of power to the computer system 1000. The storage device(s) 1010 can include one or more hard disk drives, flash drives, USB drives, optical drives, various media cards, diskettes, compact discs, and/or any combination thereof and can be directly connected to the computer system 1000 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 27 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 1000 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 1000 can also include a web server for generating and/or delivering the web pages to client computer systems.

In an exemplary embodiment, the computer system 1000 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Reuse

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
a tool driver configured to releasably and replaceably engage with a surgical tool having an elongate shaft with an end effector at a distal end of the elongate shaft, the tool driver including a plurality of motors and a plurality drive disks each configured to be simultaneously driven by at least one of the motors and thereby cause a single motion of the end effector, wherein the single motion includes any one of closing jaws of the end effector, translating a cutting element along the end effector, and rotating the end effector relative to the elongate shaft.

2. The system of claim 1, wherein the tool driver includes a shaft having a plurality of gears attached thereto at different axial positions along a longitudinal length of the shaft, the more than one of the drive disks being simultaneously driven being configured to cooperate to drive one of the gears and thereby cause the single motion of the end effector.

3. The system of claim 2, wherein, when the tool driver is releasably and replaceably engaged with the surgical tool, a longitudinal axis of the elongate shaft of the surgical tool is substantially coaxial with a longitudinal axis of the shaft of the tool driver.

4. The system of claim 2, wherein the driving of the one of the gears causes the one of the gears to rotate about a longitudinal axis of the shaft of the tool driver.

5. The system of claim 2, each of the drive disks includes a gear.

6. The system of claim 1, wherein each of the drive disks includes a rotatable gear.

7. A surgical system, comprising:
a surgical tool including an elongate shaft, an end effector at a distal end of the elongate shaft, and a plurality of actuation shafts operatively coupled to the end effector and extending along the elongate shaft, each of the actuation shafts being configured to operate a function of the end effector such that the end effector has a plurality of functions; and
a tool driver configured to releasably and replaceably operatively engage the surgical tool, the tool driver including a plurality of motors and a plurality of drive disks, two of the drive disks being configured to be simultaneously driven by respective ones of the motors and thereby actuate one of the actuation shafts and cause one of the functions of the end effector.

8. The system of claim 7, wherein the one of functions of the end effector includes any one of closing jaws of the end effector, articulating the end effector relative to the elongate shaft, translating a cutting element along the end effector, rotating the end effector relative to the elongate shaft, and rotating the elongate shaft and the end effector relative to a proximal housing of the surgical tool.

9. The system of claim 7, wherein different combinations of two drive disks among the plurality of drive disks being simultaneously driven by respective ones of the motors are configured to cause different ones of the functions of the end effector.

10. The system of claim 7, wherein when the two drive disks are driven the drive disks are each configured to rotate and thereby cause translation of the one of the actuation shafts to cause the one of the functions of the end effector.

11. The system of claim 10, wherein the rotational movement of the drive disks are transferred to the surgical tool as rotational motion, and the surgical tool includes an actuator configured to translate the rotational motion received from the tool driver to translational motion for the one of the actuation shafts.

12. The system of claim 10, wherein the rotational movement of the drive disks are transferred to the surgical tool as translational motion that causes the translation of the one of the actuation shafts.

13. The system of claim 7, wherein each of the drive disks includes a rotatable gear.

14. The system of claim 7, wherein the plurality of drive disks includes three or more drive disks, and the plurality of motors includes three or more motors.

15. A surgical method, comprising:
actuating a plurality of motors of a tool driver of a robotic surgical system and thereby simultaneously drive more than one of a plurality of drive disks of the tool driver, the driving of the more than one of the plurality of drive disks causing performance of a single function of an end effector of a surgical tool, the surgical tool including a proximal housing releasably and replaceably coupled to the tool driver, and the surgical tool including an elongate shaft extending distally from the proximal housing and having the end effector at a distal end thereof,
wherein the single function of the end effector includes any one of closing jaws of the end effector, translating a cutting element along the end effector, rotating the end effector relative to the elongate shaft, and rotating the elongate shaft and the end effector relative to the proximal housing.

16. The method of claim 15, wherein the simultaneous driving of the more than one of the plurality of drive disks causing a disk mounted on a drive shaft of the tool driver to rotate, a longitudinal axis of the drive shaft being substantially coaxial with the elongate shaft of the surgical tool.

* * * * *